United States Patent
Matsuzawa et al.

(10) Patent No.: US 8,568,770 B2
(45) Date of Patent: *Oct. 29, 2013

(54) ADHESIVE MATERIAL CONTAINING 5-METHYL-1-PHENYL-2-(1H)-PYRIDONE

(75) Inventors: Takayasu Matsuzawa, Toyama (JP); Tamaki Horiuchi, Toyama (JP); Seijiro Yama, Toyama (JP); Sunao Takeuchi, Toyama (JP); Makoto Takeuchi, Toyama (JP)

(73) Assignee: Lead Chemical Co., Ltd., Toyama-shi (JP)

( * ) Notice: Subject to any disclaimer, the term of this patent is extended or adjusted under 35 U.S.C. 154(b) by 26 days.

This patent is subject to a terminal disclaimer.

(21) Appl. No.: 13/130,461

(22) PCT Filed: Nov. 20, 2009

(86) PCT No.: PCT/JP2009/069720
§ 371 (c)(1),
(2), (4) Date: Aug. 3, 2011

(87) PCT Pub. No.: WO2010/058844
PCT Pub. Date: May 27, 2010

(65) Prior Publication Data
US 2011/0293670 A1    Dec. 1, 2011

(30) Foreign Application Priority Data
Nov. 21, 2008    (JP) ................. 2008-298785

(51) Int. Cl.
| A61L 15/16 | (2006.01) |
| A61L 15/22 | (2006.01) |
| A61L 15/30 | (2006.01) |
| A61L 15/34 | (2006.01) |
| A61F 13/00 | (2006.01) |

(52) U.S. Cl.
USPC ........... 424/447; 424/448; 424/449; 424/485; 514/345

(58) Field of Classification Search
None
See application file for complete search history.

(56) References Cited

U.S. PATENT DOCUMENTS

| 7,605,173 B2 | 10/2009 | Seth | |
| 2003/0125308 A1* | 7/2003 | Inamoto et al. | ............... 514/165 |
| 2006/0167064 A1 | 7/2006 | Seth | |

FOREIGN PATENT DOCUMENTS

| JP | A-2004-203795 | 7/2004 |
| JP | A-2006-298774 | 11/2006 |
| TW | 200418516 | 10/2004 |
| WO | WO 02/060446 A1 | 8/2002 |
| WO | WO 2004/073680 A1 | 9/2004 |
| WO | WO 2004/073713 A1 | 9/2004 |

OTHER PUBLICATIONS

Chinese Office Action issued in Chinese Application No. 200980154410.9 dated Sep. 24, 2012 (w/translation).
International Search Report issued in Application No. PCT/JP2009/069720; Dated Feb. 23, 2010.

* cited by examiner

*Primary Examiner* — Lakshmi Channavajjala
(74) *Attorney, Agent, or Firm* — Oliff & Berridge, PLC (57) ABSTRACT

There is provided an adhesive preparation containing 5-methyl-1-phenyl-2-(1H)-pyridone. The adhesive preparation is a 5-methyl-1-phenyl-2-(1H)-pyridone-containing adhesive preparation including an active medicinal ingredient-containing layer, characterized in that the active medicinal ingredient-containing layer contains an lipophilic base, a dissolving agent (except glycerin and a medium-chain aliphatic acid triglyceride), and 5-methyl-1-phenyl-2-(1H)-pyridone or medically acceptable salts thereof.

15 Claims, 6 Drawing Sheets

ADHESIVE MATERIAL CONTAINING 5-METHYL-1-PHENYL-2-(1H)-PYRIDONE

TECHNICAL FIELD

The present invention relates to an adhesive preparation containing an active medicinal ingredient-containing layer effective for prevention and remedy of skin diseases such as hypertrophic scars, keloid, contact dermatitis, contagious wart (verruca), palmoplantar pustulosis, and fibrous skin diseases. More in detail, the present invention relates to an oily adhesive preparation that is characterized by containing, as an active medicinal ingredient, 5-methyl-1-phenyl-2-(1H)-pyridone (general name: pirfenidone) or medically acceptable salts thereof at a high concentration, and that is characterized in that, as a dissolving agent, a specific compound is used.

BACKGROUND ART 5-methyl-1-phenyl-2-(1H)-pyridone (hereinafter, expressed also as PFD) is known to be useful for prevention and remedy of fibrous diseases such as pulmonary fibrosis, fibrosis hypertrophy of prostate, and nephrosclerosis, and hitherto, there have been disclosed a tablet (see Patent Document 1) containing, as the main medicinal agent, 5-methyl-1-phenyl-2-(1H)-pyridone as a medicament for remedying pulmonary fibrosis, and a solution state medicament composition (see Patent Document 2) as a medicament in another dosage form for remedying a fibrous skin disease.

However, an adhesive preparation for prevention or remedy of skin diseases using, as an active medicinal ingredient, 5-methyl-1-phenyl-2-(1H)-pyridone or medically acceptable salts thereof is unknown.

RELATED-ART DOCUMENT

Patent Document

Patent Document 1: WO 2002/060446
Patent Document 2: Japanese Patent Application Publication No. JP-A-2004-203795

DISCLOSURE OF THE INVENTION

Problem to be Solved by the Invention

Thus, the applicant of the present invention disclosed in the prior patent application (JP-A-2007-139653) an adhesive preparation containing, as an active medicinal ingredient, 5-methyl-1-phenyl-2-(1H)-pyridone or medically acceptable salts thereof in a content of 0.1 to 30% by mass, based on the total mass of an active medicinal ingredient-containing layer.

However, it was desired to further improve this disclosed PFD-containing adhesive preparation in terms of the skin permeability of the active medicinal ingredient and the persistence of the medicinal effect thereof in order to make possible more effective prevention and remedy of skin diseases.

Means for Solving the Problem

As a result of assiduous research intended to overcome these disadvantages, the inventors of the present invention have found for the first time that in an oily PFD-containing adhesive preparation in which 5-methyl-1-phenyl-2-(1H)-pyridone that is an active medicinal ingredient is dissolved at a high concentration, by using, together with an lipophilic base, a specific dissolving agent, that is, a dissolving agent other than glycerin and a medium-chain aliphatic acid triglyceride, the skin permeation effect of an active medicinal ingredient and the persistence effect of the medicinal effect thereof can be enhanced, and further that by using, as the dissolving agent, butylene glycol, polyethylene glycol, N-methyl-pyrrolidone, propylene carbonate, isopropyl myristate, crotamiton, or diisopropyl adipate, particularly crotamiton and diisopropyl adipate, the above effects can be further enhanced, and have completed the present invention.

A first aspect of the present invention relates to a 5-methyl-1-phenyl-2-(1H)-pyridone-containing adhesive preparation including an active medicinal ingredient-containing layer, characterized in that the active medicinal ingredient-containing layer contains an lipophilic base, a dissolving agent (except glycerin and a medium-chain aliphatic acid triglyceride), and 5-methyl-1-phenyl-2-(1H)-pyridone or medically acceptable salts thereof.

A second aspect of the present invention relates to the 5-methyl-1-phenyl-2-(1H)-pyridone-containing adhesive preparation according to claim 1, in which the dissolving agent is selected from a group consisting of butylene glycol, polyethylene glycol, N-methyl-pyrrolidone, propylene carbonate, isopropyl myristate, crotamiton, and diisopropyl adipate.

A third aspect of the present invention relates to the 5-methyl-1-phenyl-2-(1H)-pyridone-containing adhesive preparation according to claim 2, in which the dissolving agent is selected from a group consisting of crotamiton and diisopropyl adipate.

A fourth aspect of the present invention relates to the 5-methyl-1-phenyl-2-(1H)-pyridone-containing adhesive preparation according to any one of claims 1 to 3, in which the active medicinal ingredient-containing layer further contains a permeation enhancer.

A fifth aspect of the present invention relates to the 5-methyl-1-phenyl-2-(1H)-pyridone-containing adhesive preparation according to any one of claims 1 to 3 containing 5-methyl-1-phenyl-2-(1H)-pyridone or medically acceptable salts thereof in an amount of 3 to 20% by mass, based on the total amount of the active medicinal ingredient-containing layer.

Effects of the Invention

The 5-methyl-1-phenyl-2-(1H)-pyridone-containing adhesive preparation of the present invention is highly effective in skin permeability of the active medicinal ingredient by using, as the dissolving agent, a specific dissolving agent, that is, a dissolving agent other than glycerin and a medium-chain aliphatic acid triglyceride, under a condition of dissolving 5-methyl-1-phenyl-2-(1H)-pyridone that is an active medicinal ingredient at a high concentration relative to an lipophilic base, particularly in an amount of 3 to 20% by mass, based on the total amount of the active medicinal ingredient-containing layer.

With respect to the enhancing effect of the skin permeability by the active medicinal ingredient, particularly by using, as the dissolving agent, butylene glycol, polyethylene glycol, N-methyl-pyrrolidone, propylene carbonate, isopropyl myristate, crotamiton, or diisopropyl adipate, a higher effect can be obtained.

Further, among these dissolving agents, by using crotamiton and diisopropyl adipate, the skin permeability of the active medicinal ingredient can be dramatically enhanced.

In the 5-methyl-1-phenyl-2-(1H)-pyridone-containing adhesive preparation of the present invention, by blending 5-methyl-1-phenyl-2-(1H)-pyridone that is an active medicinal ingredient in the base at a high concentration, it is considered that even when a part of the active medicinal ingredient is consumed by skin permeation, and consequently, the amount of the active medicinal ingredient in the base is reduced, the active medicinal ingredient in a solid state (powder) gradually dissolves, so that it becomes such a condition that a saturated state of the active medicinal ingredient can be maintained. It has become apparent that as the result thereof, the effect that the medicinal effect persists over a long period is exerted.

Accordingly, by using the 5-methyl-1-phenyl-2-(1H)-pyridone-containing adhesive preparation of the present invention, there can be effectively prevented or remedied skin diseases such as hypertrophic scars, keloid, contact dermatitis, contagious wart (verruca), palmoplantar pustulosis, and fibrous skin diseases.

Moreover, by using the 5-methyl-1-phenyl-2-(1H)-pyridone-containing adhesive preparation of the present invention in combination with a permeation enhancer, together with the above specific dissolving agent, the skin permeability of the active medicinal ingredient can be much more enhanced.

BEST MODES FOR CARRYING OUT THE INVENTION

The active medicinal ingredient of the adhesive preparation of the present invention is 5-methyl-1-phenyl-2-(1H)-pyridone.

5-methyl-1-phenyl-2-(1H)-pyridone that is the active medicinal ingredient may be in the form of medically acceptable salts thereof.

Examples of such salts include acid addition salts with an acid such as hydrochloric acid, sulfuric acid, phosphoric acid, para-toluenesulfonic acid, and methanesulfonic acid, and salts with an alkali such as sodium salts and potassium salts.

In the adhesive preparation of the present invention, although the blending amount of the active medicinal ingredient varies depending on the formulation, the active medicinal ingredient is desirably blended in an amount of 3 to 20% by mass, based on the total amount of the active medicinal ingredient-containing layer.

The dissolving agent used for the adhesive preparation of the present invention is a dissolving agent generally used for an lipophilic base except glycerin and a medium-chain aliphatic acid triglyceride and is preferably selected from a group consisting of butylene glycol, polyethylene glycol, N-methyl-pyrrolidone, propylene carbonate, isopropyl myristate, crotamiton, and diisopropyl adipate, most preferably from a group consisting of crotamiton and diisopropyl adipate.

These dissolving agents may be used individually or in an appropriate combination of two or more types thereof. The blending amount of the dissolving agent is about 0.1 to 20% by mass, based on the total amount of the active medicinal ingredient-containing layer.

The base of the adhesive preparation of the present invention is an lipophilic base. As the lipophilic base, for example, an lipophilic base produced by mixing a component 1): lipophilic polymer, a component 2): plasticizer, and a component 3): tackifier may be used.

Examples of the component 1): lipophilic polymer include styrene/isoprene/styrene block copolymers, styrene/butadiene block copolymers, polyisobutylene, crude rubber, polyisoprene, and polybutene, to which the examples are not limited. These lipophilic polymers may be used individually or in an appropriate combination of two or more types thereof. The blending amount of the lipophilic polymer is about 10 to 50% by mass, based on the total amount of the active medicinal ingredient-containing layer.

Examples of the component 2): plasticizer include liquid paraffin, vegetable oils, animal oils, polybutene, low molecular weight polyisobutylene, vaseline, lanolin, and higher aliphatic esters, to which the examples are not limited. These plasticizers may be used individually or in an appropriate combination of two or more types thereof. The blending amount of the plasticizer is about 10 to 50% by mass, based on the total amount of the active medicinal ingredient-containing layer.

Examples of the component 3): tackifier include petroleum resins, rosin-based resins, hydrogenated rosins, rosin esters, terpene resins, modified terpene resins, aromatic hydrocarbon resins, and aliphatic hydrocarbon resins, to which the examples are not limited. These tackifiers may be used individually or in an appropriate combination of two or more types thereof. The blending amount of the tackifier is about 5 to 50% by mass, based on the total amount of the active medicinal ingredient-containing layer.

Preferably, the lipophilic base contains 10 to 40% by mass of the lipophilic polymer, 10 to 40% by mass of the plasticizer, and 5 to 40% by mass of the tackifier, based on the total amount of the lipophilic base.

Preferably, in the active medicinal ingredient-containing layer of the adhesive preparation of the present invention, for further enhancing the skin permeability of the active medicinal ingredient, a permeation enhancer together with the above specific dissolving agent is blended.

Although examples of the permeation enhancer are not particularly limited so long as the permeation enhancer is commonly used for a conventional transdermal preparation, examples include alcohols, aliphatic acids, aliphatic esters, aliphatic ethers, lactic esters, acetic esters, terpene-based compounds, pyrrolidone derivatives, organic acids, organic acid esters, essential oils, hydrocarbons, propylene carbide, azone, and derivatives thereof.

Further, specific examples of the permeation enhancer include ethanol, lauryl alcohol, myristyl alcohol, cetyl alcohol, cyclodextrin, calcium thioglycolate, ethyl lactate, cetyl lactate, lactic acid, urea, 1-menthol, d-limonene, and dl-camphor.

These permeation enhancers may be used individually or in an appropriate combination of two or more types thereof. The blending amount of the permeation enhancer is about 0.1 to 20% by mass, based on the total amount of the active medicinal ingredient-containing layer.

In the active medicinal ingredient-containing layer of the adhesive preparation of the present invention, there may also be blended, besides 5-methyl-1-phenyl-2-(1H)-pyridone or medically acceptable salts thereof that are the active medicinal ingredient, the dissolving agent, the lipophilic base, and, if necessary, various other additives such as tackifiers, softeners, antioxidants, age resistors, preservatives, flavoring agents, pH adjusters, emulsifiers, dispersants, stabilizers, antiseptics, and excipients, which are commonly used for a conventional transdermal preparation.

Examples of the tackifier include silicone rubbers, polyisobutylene rubbers, acrylic rubbers, and natural oily adhesive substances, to which the examples are not limited. These tackifiers may be used individually or in an appropriate combination of two or more types thereof. The blending amount of the tackifier is about 5 to 50% by mass, based on the total amount of the active medicinal ingredient-containing layer.

Examples of the softener include liquid paraffin, polybutene, castor oil, cotton seed oil, palm oil, coconut oil, and process oil, to which the examples are not limited. These softeners may be used individually or in an appropriate combination of two or more types thereof. The blending amount of the softener is about 1 to 50% by mass, based on the total amount of the active medicinal ingredient-containing layer.

Examples of the antioxidant include ascorbic acid, palmitic acid, ascorbic acid, sodium hydrogen sulfite, sodium edetate, tetra-sodium edetate, dry sodium sulfite, citric acid, sodium citrate, tocopherol acetate, dl-α-tocopherol, potassium dichloroisocyanurate, dibutylhydroxytoluene, butylhydroxyanisole, soybean lecithin, sodium pyrosulfite, benzotriazole, pentaerythryl-tetrakis[3-(3,5-di-tert-butyl-4-hydroxyphenyl)propionate], propyl gallate, and 2-mercaptobenzimidazole, to which the examples are not limited. These antioxidants may be used individually or in an appropriate combination of two or more types thereof. The blending amount of the antioxidant is about 0.005 to 20% by mass, based on the total amount of the active medicinal ingredient-containing layer.

Examples of the age resistor include: amino acids such as glycine, proline, hydroxyproline, leucine, alanine, γ-aminobutyric acid, and ε-aminocaproic acid; vitamins such as retinol, thiamine, riboflavin, pyridoxine hydrochloride, and pantothenic acid; hydroxy acids such as glycolic acid, lactic acid, and salicylic acid; tannin; flavonoid; saponin; allantoin; and components, extracts, and essential oils derived from plants such as camomile, licorice, Anthemis nobilis, carrot, and rice, to which the examples are not limited. These age resistors may be used individually or in an appropriate combination of two or more types thereof. The blending amount of the age resistor is about 0.005 to 20% by mass, based on the total amount of the active medicinal ingredient-containing layer.

Examples of the preservative include methyl para-hydroxybenzoate, ethyl para-hydroxybenzoate, propyl para-hydroxybenzoate, chlorobutanol, and benzyl alcohol, to which the examples are not limited. These preservatives may be used individually or in an appropriate combination of two or more types thereof. The blending amount of the preservative is about 0.005 to 5% by mass, based on the total amount of the active medicinal ingredient-containing layer.

Examples of the flavoring agent include: perfumery materials such as benzyl, linalyl acetate, amyl acetate, benzaldehyde, cinnamic aldehyde, citronellal, menthol, citral, and cis-jasmon; and medicinal substances such as methyl salicylate, camphor, and cresol. These flavoring agents may be used individually or in an appropriate combination of two or more types thereof. The blending amount of the flavoring agent is about 0.05 to 5% by mass, based on the total amount of the active medicinal ingredient-containing layer.

Although the pH adjuster is not particularly limited so long as the pH adjuster is a pH adjuster commonly used for a conventional transdermal preparation, examples thereof include: inorganic acids such as hydrochloric acid, sulfuric acid, nitric acid, hydrobromic acid, and phosphoric acid, and salts thereof; organic acids such as acetic acid, succinic acid, fumaric acid, malic acid, oxalic acid, lactic acid, glutaric acid, salicylic acid, and tartaric acid, and salts thereof; aliphatic acids such palmitic acid, stearic acid, oleic acid, and linolic acid, and salts thereof; inorganic bases such sodium hydroxide and calcium hydroxide; and organic bases such as ammonia, diiospropanolamine, diethanolamine, triethanolamine, and triethylamine. These pH adjusters may be used individually or in an appropriate combination of two or more types thereof. The blending amount of the pH adjuster is about 0.05 to 10% by mass, based on the total amount of the active medicinal ingredient-containing layer.

Examples of the emulsifier include sorbitan monooleate, polyacrylic acid, polyacrylamide, polyN-vinylpyrrolidone, chitin, chitosan, and cellulose, to which the examples are not limited. These emulsifiers may be used individually or in an appropriate combination of two or more types thereof. The blending amount of the emulsifier is about 0.05 to 10% by mass, based on the total amount of the active medicinal ingredient-containing layer.

Although examples of the dispersant are not particularly limited so long as the dispersant enhances the dispersibility of various components in the active medicinal ingredient-containing layer, examples include synthesized aluminum silicate, hydrous aluminum silicate, aluminum hydroxide, magnesium silicate, zinc oxide, titanium oxide, and aliphatic acid metal salts such as a stearic acid metal salt. These dispersants may be used individually or in an appropriate combination of two or more types thereof. The blending amount of the dispersant is about 0.5 to 50% by mass, based on the total amount of the active medicinal ingredient-containing layer.

As the stabilizer, for example, the agents exemplified above as the pH adjuster can be used. Further, examples of the stabilizer also include sodium hydrogen sulfite, ascorbic acid, sodium ascorbate, butylhydroxyanisole, dibutylhydroxytoluene, propyl gallate, tocopherol acetate, and D-α-tocopherol. These stabilizers may be used individually or in an appropriate combination of two or more types thereof. The blending amount of the stabilizer is about 0.005 to 20% by mass, based on the total amount of the active medicinal ingredient-containing layer.

Examples of the antiseptic include methylparaben, ethylparaben, propylparaben, butylparaben, and phenoxyethanol, to which the examples are not limited. These antiseptics may be used individually or in an appropriate combination of two or more types thereof. The blending amount of the antiseptic is about 0.005 to 5% by mass, based on the total amount of the active medicinal ingredient-containing layer.

Examples of the excipient include: saccharides such as glucose, fructose, galactose, mannose, palatinose, sucrose, maltose, lactose, trehalose, oligosaccharides, and dextrin; and celluloses such as crystalline cellulose, methyl cellulose, carboxymethyl cellulose or salts thereof, hydroxypropyl cellulose, and hydroxypropylmethyl cellulose, to which the examples are not limited. These excipients may be used individually or in an appropriate combination of two or more types thereof. The blending amount of the excipient is about 0.1 to 40% by mass, based on the total amount of the active medicinal ingredient-containing layer.

The adhesive preparation of the present invention may be in a form of various adhesive preparations such as a poultice, a plaster preparation, and a tape preparation according to the application thereof. The adhesive preparation of the present invention can be produced by, for example, applying a mixture in which 5-methyl-1-phenyl-2-(1H)-pyridone and a dissolving agent each in a predetermined amount are blended with an lipophilic base (transdermal preparation) on an appropriate support medium in a predetermined thickness to form an active medicinal ingredient-containing layer; coating the active medicinal ingredient-containing layer with a predetermined liner; and cutting out the resultant laminate into a desired size. The adhesive preparation of the present invention may also be formed, depending on the production method thereof, by, for example, first applying a base (transdermal preparation) containing 5-methyl-1-phenyl-2-(1H)-pyridone and a dissolving agent on a liner to form an active medicinal ingredient-containing layer; coating the active medicinal ingredient-containing layer with a support medium; and transferring the active medicinal ingredient-containing layer onto the support medium.

The adhesive preparation of the present invention is an adhesive preparation directly contacted with an affected area, so that after the adhesive preparation is produced as described above, it is preferable that the produced adhesive preparation is subjected to sterilization treatment. Although the sterilization method is not particularly limited so long as the method is a method commonly used for a sterilization of a conventional medicament, examples thereof include a γ-ray sterilization method, an electron beam sterilization method, a high pressure vapor sterilization method, and an ethylene oxide gas sterilization method.

The support medium used for the adhesive preparation of the present invention is not particularly limited and a common-purpose material can be used as the support medium for the adhesive preparation. As the support medium, there are used, for example, woven clothes, nonwoven clothes, sheets, films, or laminates thereof of a natural or synthesized polymer, preferably vinyl chloride films, polyethylene-based films, ethylene copolymer films, polypropylene-based films, polyurethane, further woven clothes and nonwoven clothes, and laminates thereof with plastics.

The size, shape, thickness, and the like of the support medium are accordingly selected.

The liner used for the adhesive preparation of the present invention is not particularly limited and a common-purpose material as the liner for the adhesive preparation can be used. Examples of the liner include sheets, films, and laminates thereof of a natural or synthesized polymer, and preferred examples thereof include peeling papers subjected to treatment (such as coating with synthesized polymers) for making the peeling easy and sheets, films, and laminates thereof of cellophane, polyethylene, polyethylene terephthalate, polypropylene, polyester, and polyvinylidene chloride.

Hereinafter, the usefulness of the present invention will be described referring to Examples and Test Examples that should not be construed as limiting the scope of the present invention. Here, unless defined otherwise, "part" is based on the mass.

EXAMPLES

Example 1

10 parts of polyisobutylene, 20 parts of styrene/isoprene/styrene block copolymer, 0.5 parts of dibutylhydroxytoluene, 18 parts of liquid paraffin, and 11.5 parts of hydrogenated rosin glycerin ester were dissolved in hexane in the equivalent amount (corresponding to 100 parts) to the total amount of the active medicinal ingredient-containing layer (solution A). 20 parts of 5-methyl-1-phenyl-2-(1H)-pyridone as the active medicinal ingredient was mixed with 10 parts of liquid paraffin and 10 parts of 1,3-butylene glycol (dissolving agent) (solution B). The solution B was added to the solution A and the resultant mixture was homogeneously mixed. The thus obtained mixture was spread on a polyester film (liner) subjected to silicone treatment and hexane was volatilized-removed to form an active medicinal ingredient-containing layer, followed by coating the active medicinal ingredient-containing layer with a polyester nonwoven cloth (support medium). The resultant laminate was cut out into a desired size to obtain the adhesive preparation of Example 1 containing 20% of 5-methyl-1-phenyl-2-(1H)-pyridone.

Example 2

In substantially the same manner as in Example 1, except that the amount of 5-methyl-1-phenyl-2-(1H)-pyridone that is an active medicinal ingredient was changed to 3 parts (with respect to the amounts of other components, see Table 1 below), the adhesive preparation of Example 2 containing 3% of 5-methyl-1-phenyl-2-(1H)-pyridone was obtained.

Example 3

In substantially the same manner as in Example 1, except that the amount of 5-methyl-1-phenyl-2-(1H)-pyridone that is an active medicinal ingredient was changed to 5 parts (with respect to the amounts of other components, see Table 1 below), the adhesive preparation of Example 3 containing 5% of 5-methyl-1-phenyl-2-(1H)-pyridone was obtained.

Example 4

In substantially the same manner as in Example 1, except that the amount of 5-methyl-1-phenyl-2-(1H)-pyridone that is an active medicinal ingredient was changed to 10 parts (with respect to the amounts of other components, see Table 1 below), the adhesive preparation of Example 4 containing 10% of 5-methyl-1-phenyl-2-(1H)-pyridone was obtained.

Example 5

In substantially the same manner as in Example 1, except that, as the dissolving agent, polyethylene glycol 400 was used instead of 1,3-butylene glycol (with respect to the amount of each component, see Table 1 below), the adhesive preparation of Example 5 containing 20% of 5-methyl-1-phenyl-2-(1H)-pyridone was obtained.

Example 6

In substantially the same manner as in Example 1, except that, as the dissolving agent, N-methyl-pyrrolidone was used instead of 1,3-butylene glycol (with respect to the amount of each component, see Table 1 below), the adhesive preparation of Example 6 containing 20% of 5-methyl-1-phenyl-2-(1H)-pyridone was obtained.

Example 7

In substantially the same manner as in Example 1, except that, as the dissolving agent, propylene carbonate was used instead of 1,3-butylene glycol (with respect to the amount of each component, see Table 1 below), the adhesive preparation of Example 7 containing 20% of 5-methyl-1-phenyl-2-(1H)-pyridone was obtained.

Example 8

In substantially the same manner as in Example 1, except that, as the dissolving agent, isopropyl myristate was used instead of 1,3-butylene glycol (with respect to the amount of each component, see Table 1 below), the adhesive preparation of Example 8 containing 20% of 5-methyl-1-phenyl-2-(1H)-pyridone was obtained.

Example 9

In substantially the same manner as in Example 1, except that, as the dissolving agent, crotamiton was used instead of 1,3-butylene glycol (with respect to the amount of each component, see Table 1 below), the adhesive preparation of Example 9 containing 20% of 5-methyl-1-phenyl-2-(1H)-pyridone was obtained.

Example 10

In substantially the same manner as in Example 1, except that, as the dissolving agent, diisopropyl adipate was used instead of 1,3-butylene glycol (with respect to the amount of each component, see Table 1 below), the adhesive preparation of Example 10 containing 20% of 5-methyl-1-phenyl-2-(1H)-pyridone was obtained.

Example 11

In substantially the same manner as in Example 1, except that, besides the dissolving agent, 4 parts of 1-menthol was further used as a permeation enhancer (with respect to the amount of each component, see Table 1 below), the adhesive preparation of Example 11 containing 20% of 5-methyl-1-phenyl-2-(1H)-pyridone was obtained.

Comparative Example 1

In substantially the same manner as in Example 1, except that no dissolving agent was used (with respect to the amount of each component, see Table 1 below), the adhesive preparation of Comparative Example 1 containing 20% of 5-methyl-1-phenyl-2-(1H)-pyridone was obtained.

Comparative Example 2

In substantially the same manner as in Example 1, except that, as the dissolving agent, concentrated glycerin was used instead of 1,3-butylene glycol (with respect to the amount of each component, see Table 1 below), the adhesive preparation of Comparative Example 2 containing 20% of 5-methyl-1-phenyl-2-(1H)-pyridone was obtained.

Comparative Example 3

In substantially the same manner as in Example 1, except that, as the dissolving agent, a medium-chain aliphatic acid triglyceride was used instead of 1,3-butylene glycol (with respect to the amount of each component, see Table 1 below), the adhesive preparation of Comparative Example 3 containing 20% of 5-methyl-1-phenyl-2-(1H)-pyridone was obtained.

TABLE 1

Examples and Comparative Examples: Preparation Formulation List

| Blended components | | Example 1 | Example 2 | Example 3 | Example 4 | Example 5 | Example 6 | Example 7 | Example 8 | Example 9 | Example 10 | Example 11 | Comp. Example 1* | Comp. Example 2* | Comp. Example 3* |
|---|---|---|---|---|---|---|---|---|---|---|---|---|---|---|---|
| Base | Polyisobutylene | 10 | 12.5 | 12 | 11.5 | 10 | 10 | 10 | 10 | 10 | 10 | 9.5 | 11.5 | 10 | 10 |
| | Styrene/isoprene/styrene block copolymer | 20 | 25 | 24.5 | 23 | 20 | 20 | 20 | 20 | 20 | 20 | 19 | 23 | 20 | 20 |
| | Hydrogenated rosin glycerin ester | 11.5 | 14 | 14 | 13 | 11.5 | 11.5 | 11.5 | 11.5 | 11.5 | 11.5 | 11 | 13 | 11.5 | 11.5 |
| | Liquid paraffin | 28 | 35 | 34 | 32 | 28 | 28 | 28 | 28 | 28 | 28 | 26 | 32 | 28 | 28 |
| | Dibutyl hydroxy toluene | 0.5 | 0.5 | 0.5 | 0.5 | 0.5 | 0.5 | 0.5 | 0.5 | 0.5 | 0.5 | 0.5 | 0.5 | 0.5 | 0.5 |
| Dissolving agent | 1,3-butylene glycol | 10 | 10 | 10 | 10 | — | — | — | — | — | — | 10 | — | — | — |
| | Concentrated glycerin | — | — | — | — | — | — | — | — | — | — | — | — | 10 | — |
| | Medium-chain aliphatic acid triglyceride (tri-ester) | — | — | — | — | — | — | — | — | — | — | — | — | — | 10 |
| | Polyethylene glycol 400 | — | — | — | — | 10 | — | — | — | — | — | — | — | — | — |
| | N-methyl-pyrrolidone | — | — | — | — | — | 10 | — | — | — | — | — | — | — | — |
| | Propylene carbonate | — | — | — | — | — | — | 10 | — | — | — | — | — | — | — |
| | Isopropyl myristate | — | — | — | — | — | — | — | 10 | — | — | — | — | — | — |
| | Crotamiton | — | — | — | — | — | — | — | — | 10 | — | — | — | — | — |
| | Diisopropyl adipate | — | — | — | — | — | — | — | — | — | 10 | — | — | — | — |

TABLE 1-continued

Examples and Comparative Examples: Preparation Formulation List

| Blended components | | Example 1 | Example 2 | Example 3 | Example 4 | Example 5 | Example 6 | Example 7 | Example 8 | Example 9 | Example 10 | Example 11 | Comp. Example 1* | Comp. Example 2* | Comp. Example 3* |
|---|---|---|---|---|---|---|---|---|---|---|---|---|---|---|---|
| Permeation enhancer | 1-menthol | — | — | — | — | — | — | — | — | — | — | 4 | — | — | — |
| Medicament (active ingredient) | 5-methyl-1-phenyl-2-(1H)-pyridone | 20 | 3 | 5 | 10 | 20 | 20 | 20 | 20 | 20 | 20 | 20 | 20 | 20 | 20 |
| | Total | 100 | 100 | 100 | 100 | 100 | 100 | 100 | 100 | 100 | 100 | 100 | 100 | 100 | 100 |

(W/W)
*Comp. means "Cmparative".

Test Example 1

In Vitro Skin Permeation Test

1) Test Method

Under pentobarbital sodium anesthesia, an abdomen skin of a hairless rat (HWY/Slc, male, 7-week old) was cut off, and from the skin, fat on the skin dermis side was carefully removed. The skin was affixed on a vertical diffusion cell through which water of 37° C. was circulated beforehand with the dermis side of the skin facing downward, and on the central portion of the skin, each of the adhesive preparations produced in Examples 1 to 11 and Comparative Examples 1 to 3 that was punched out into a circular form having a diameter of 1 cm was applied, pinched with a cell for fixation, and fixed with a clamp. Next, a receiver solution (physiological saline) that was kept warm in a thermostat bath of 37° C. was introduced into the dermis side, and the receiver solution was stirred with a magnetic stirrer. Then, over the time course, a certain volume of the receiver solution was obtained as a sample, and a receiver solution of the same volume was supplied for refill. The amount of the active medicinal ingredient (5-methyl-1-phenyl-2-(1H)-pyridone) in the obtained sample was determined quantitatively by a high performance liquid chromatography (HPLC) using the conditions described below, to thereby calculate the cumulative skin permeated amount and the skin permeating rate of 5-methyl-1-phenyl-2-(1H)-pyridone. The results thereof are shown in FIG. 1 to FIG. 6.

Here, the skin permeating rate of 5-methyl-1-phenyl-2-(1H)-pyridone was calculated by dividing the amount of PFD that permeated the skin during the interval between the receiver solution sampling times (unit time) by the unit time.

To sum up, the skin permeating rate of PFD can be calculated from the equation below.

$$\text{(Skin permeating rate of PFD)} = (R2-R1)/(t2-t1)$$

(where t1 and t2 are sampling times of receiver solution (t2>t1); and R1 and R2 are the cumulative skin permeated amount at t1 and t2, respectively)

<HPLC Conditions>
Column: Hypersil gold 4.6×150 mm 5 µm
Column temp.: 40° C.
Flow rate: 1 mL/min
Detection Wavelength: 318 nm
Injecting amount: 10 µL
Mobile phase: 0.1% formic acid/acetonitrile (17:8)

2) Results (1) Variation of Cumulative Skin Permeated Amount According to Difference of Content of Active Medicinal Ingredient (5-methyl-1-phenyl-2-(1H)-pyridone)

Figure 1:
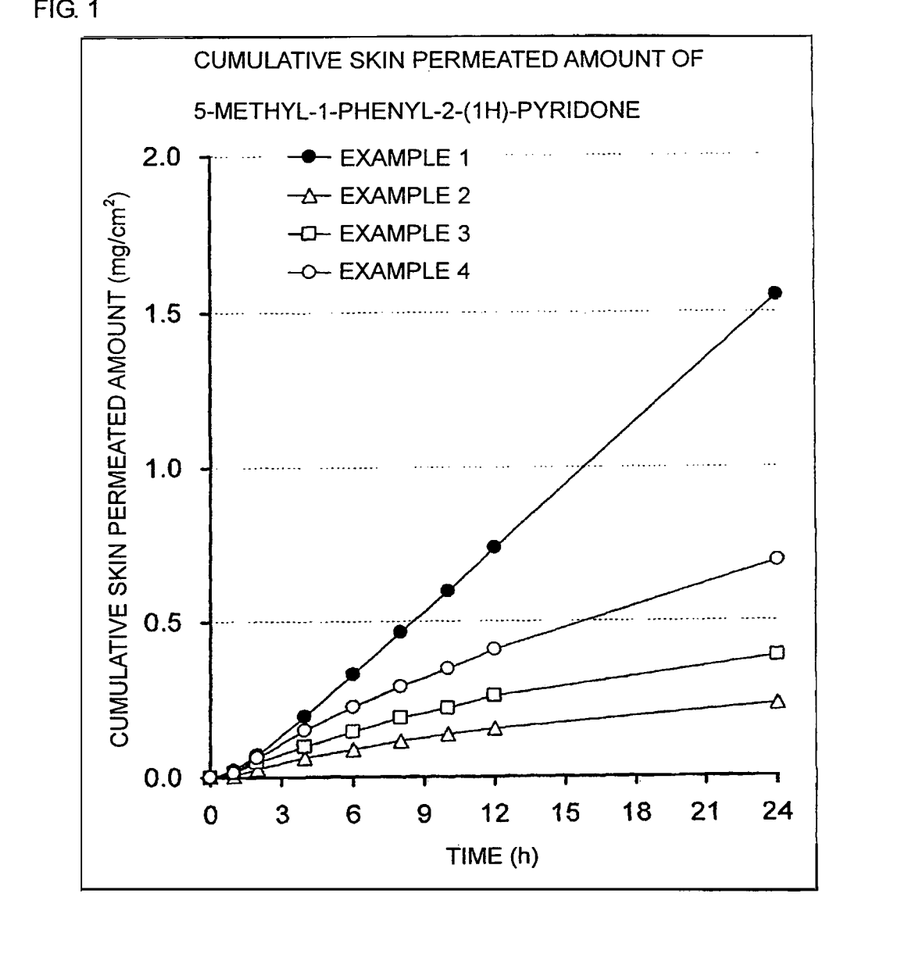
FIG. 1 is a graph showing a relationship between the elapsed time and the cumulative permeated amount of PFD after each of the PFD-containing adhesive preparations of Examples 1 to 4 was applied to the skin of a rat.

It is apparent from FIG. 1 that in the order of the adhesive preparation of Example 1, the adhesive preparation of Example 4, the adhesive preparation of Example 3, and the adhesive preparation of Example 2, that is, as the content of 5-methyl-1-phenyl-2-(1H)-pyridone that is an active medicinal ingredient in the adhesive preparation increases, the cumulative skin permeated amount increases.

Thus, it can be mentioned that with respect to the PFD-containing adhesive preparation of the present invention using a specific dissolving agent, the higher the concentration of 5-methyl-1-phenyl-2-(1H)-pyridone that is an active medicinal ingredient in the adhesive preparation is, the higher the skin permeability becomes and the longer the medicinal effect thereof persists.

Here, an excellent effect for this skin permeability and this persistence of the medicinal effect is considered to be by the virtue of that in the PFD-containing adhesive preparation of the present invention in which PFD having a low solubility in the base is blended at a high concentration, a part of PFD remains undissolved in a solid state in the base, and consequently, even when PFD is consumed by the skin permeation and the amount of PFD in the base is reduced, PFD in a solid state is gradually dissolved, so that the concentration of PFD in the base can be constantly maintained in a saturated state.

(2) Variation of Skin Permeating Rate According to Difference of Content of Active Medicinal Ingredient (5-methyl-1-phenyl-2-(1H)-pyridone)

Figure 2:
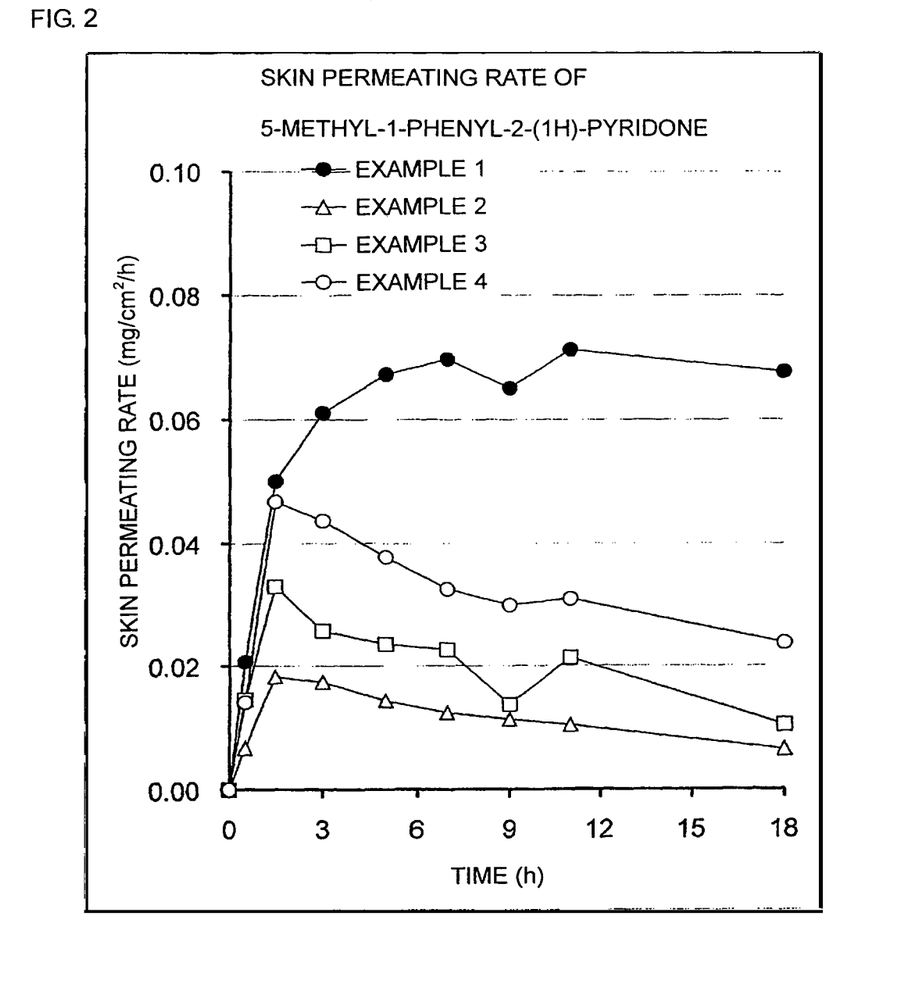
FIG. 2 is a graph showing a relationship between the elapsed time and the skin permeating rate after each of the PFD-containing adhesive preparations of Examples 1 to 4 was applied to the skin of a rat.

As shown in FIG. 2, in the order of the adhesive preparation of Example 1, the adhesive preparation of Example 4, the adhesive preparation of Example 3, and the adhesive preparation of Example 2, that is, as the content of the active medicinal ingredient in the adhesive preparation increased, the skin permeating rate of the active medicinal ingredient increased.

Thus, with respect to the PFD-containing adhesive preparation of the present invention in which 5-methyl-1-phenyl-2-(1H)-pyridone having a low solubility in the base is blended at a high concentration and a specific dissolving agent is used, as the concentration of PFD that is the active medicinal ingredient in the adhesive preparation increases, the fast-acting property of the adhesive preparation is more expected.

Figure 3:
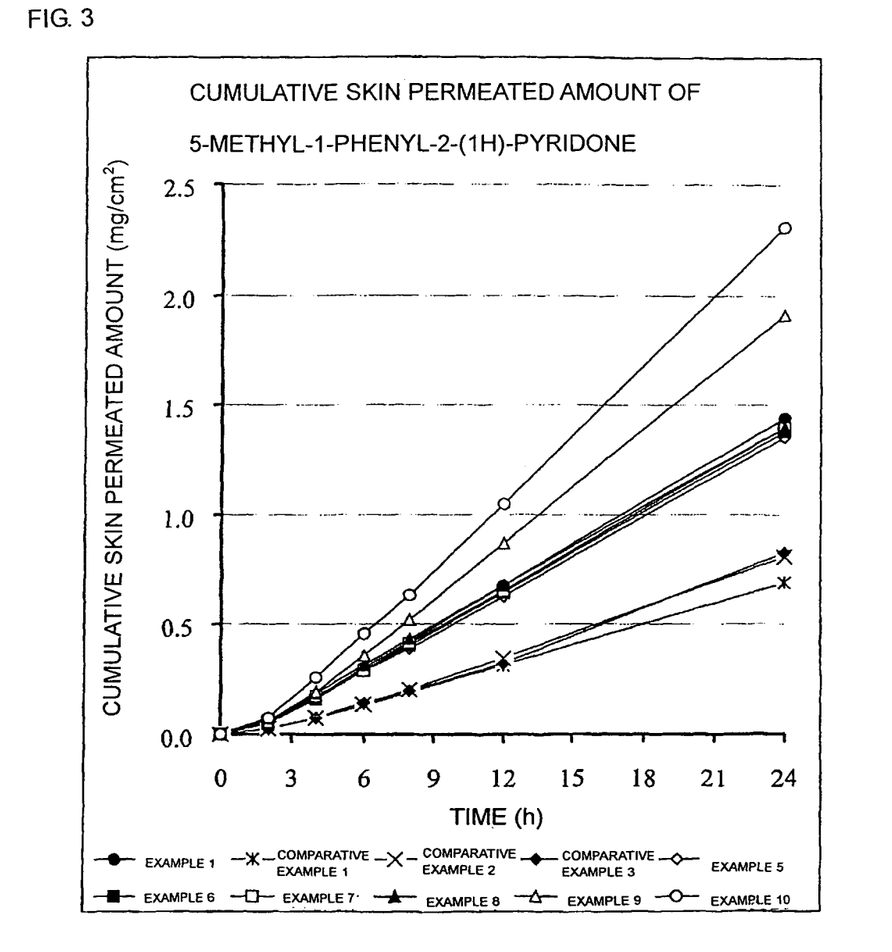
FIG. 3 is a graph showing a relationship between the elapsed time and the cumulative permeated amount of PFD after each of the PFD-containing adhesive preparations of Examples 1, 5 to 10 and Comparative Examples 1 to 3 was applied to the skin of a rat.

(3) Variation of Cumulative Skin Permeated Amount According to Difference of Type of Used Dissolving Agent As shown in FIG. 3, in comparison with the PFD-containing adhesive preparation of Comparative Example 1 containing no dissolving agent and the adhesive preparations of Comparative Example 2 and Comparative Example 3 using, as the dissolving agent, dissolving agents other than the dissolving agents of the present invention, that is, glycerin and a medium-chain aliphatic acid triglyceride, respectively, the PFD-containing adhesive preparations of the present invention of Examples 1 to 8 using, as the dissolving agent, 1,3-butylene glycol, polyethylene glycol 400, N-methyl-pyrrolidone, propylene carbonate, and isopropyl myristate exhibited a cumulative skin permeated amount of the active medicinal ingredient during half a day or one day after the application of the preparation on the skin that was about two times those of the adhesive preparations of the above Comparative Examples.

Further, the PFD-containing adhesive preparations of the present invention of Examples 9 and 10 using, as the dissolving agent, crotamiton and diisopropyl adipate, respectively, exhibited a cumulative skin permeated amount of the active medicinal ingredient during half a day or one day after the application of the preparation on the skin that was far larger than those of the PFD-containing adhesive preparations of the present invention of Examples 1 to 8.

Thus, it has become apparent that with respect to enhancing the skin permeability of the active medicinal ingredient and the persistence of the medicinal effect thereof, among a number of dissolving agents used for an oily adhesive preparation, butylene glycol, polyethylene glycol, N-methyl-pyrrolidone, propylene carbonate, and isopropyl myristate are highly effective and crotamiton and diisopropyl adipate are even further effective.

Figure 4:
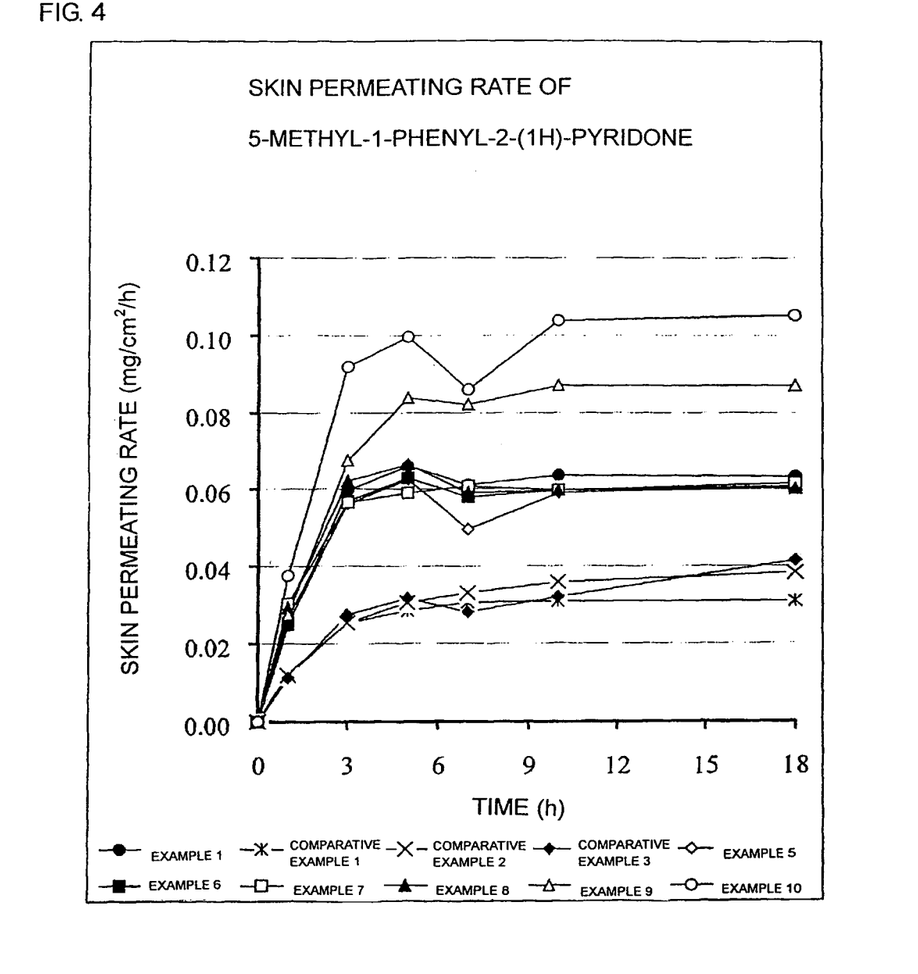
FIG. 4 is a graph showing a relationship between the elapsed time and the skin permeating rate after each PFD of Examples 1, 5 to 10 and Comparative Examples 1 to 3 was applied to the skin of a rat.

(4) Variation of Skin Permeating Rate According to Difference of Type of Used Dissolving Agent As shown in FIG. 4, in comparison with the adhesive preparation of Comparative Example 1 containing no dissolving agent and the adhesive preparations of Comparative Example 2 and Comparative Example 3 using, as the dissolving agent, dissolving agents other than the dissolving agents of the present invention, that is, glycerin and a medium-chain aliphatic acid triglyceride, respectively, the adhesive preparations of Examples 1 to 8 using, as the dissolving agent, 1,3-butylene glycol, polyethylene glycol 400, N-methyl-pyrrolidone, propylene carbonate, and isopropyl myristate, which are the dissolving agents of the present invention, exhibited a higher skin permeating rate, and further, the adhesive preparations of Examples 9 and 10 using crotamiton and diisopropyl adipate, respectively, which are the dissolving agents of the present invention, exhibited an even higher skin permeating rate.

Thus, it has become apparent that with respect to enhancing the fast-acting property of the medicament (active medicinal ingredient), among a number of dissolving agents used for an oily adhesive preparation, butylene glycol, polyethylene glycol, N-methyl-pyrrolidone, propylene carbonate, and isopropyl myristate, which are the dissolving agents of the present invention, are highly effective, and particularly, crotamiton and diisopropyl adipate are even further effective.

(5) Variation of Cumulative Skin Permeated Amount by Using Permeation Enhancer

Figure 5:
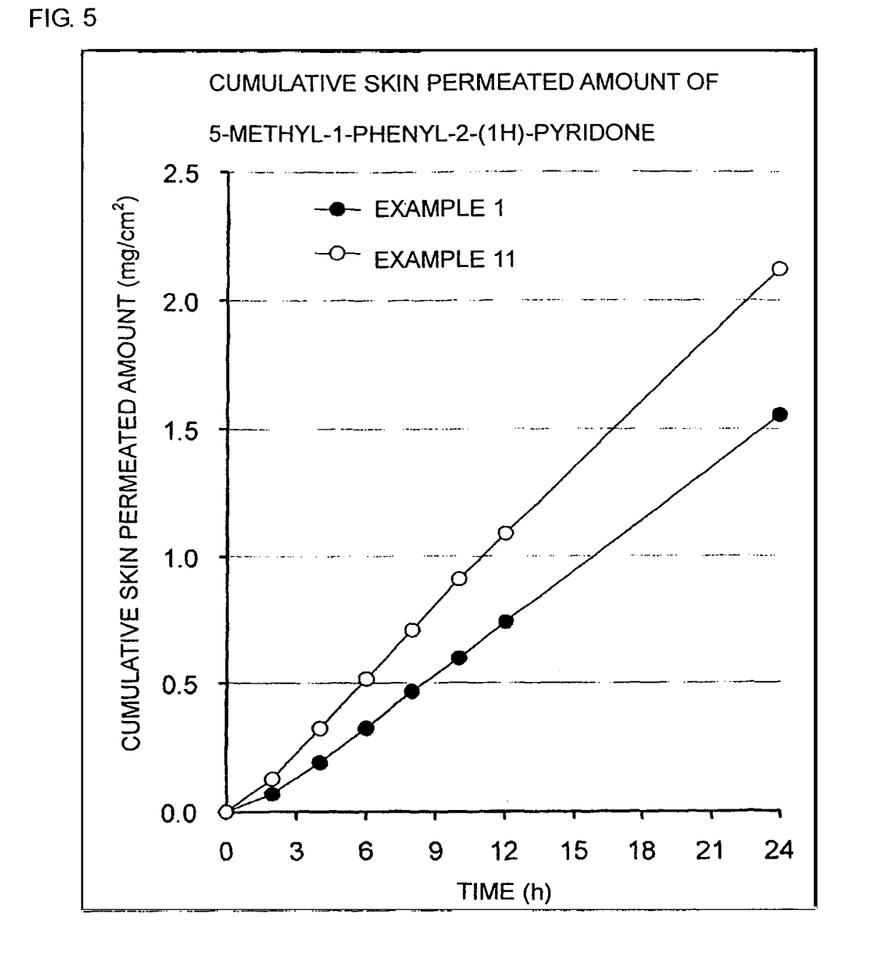
FIG. 5 is a graph showing a relationship between the elapsed time and the cumulative permeated amount of PFD after each of the PFD-containing adhesive preparations of Example 1 and Example 11 was applied to the skin of a rat.

From FIG. 5, it is apparent that in comparison with the adhesive preparation of Example 1 containing no permeation enhancer, the adhesive preparation of Example 11 using, besides the dissolving agent of the present invention, a permeation enhancer exhibited a larger cumulative skin permeated amount.

Thus, it has become apparent that by using a permeation enhancer in combination with the dissolving agent of the present invention, the skin permeability of the active medicinal ingredient and the persistence of the medicinal effect thereof are further enhanced.

(6) Variation of Skin Permeating Rate by Using Permeation Enhancer

Figure 6:
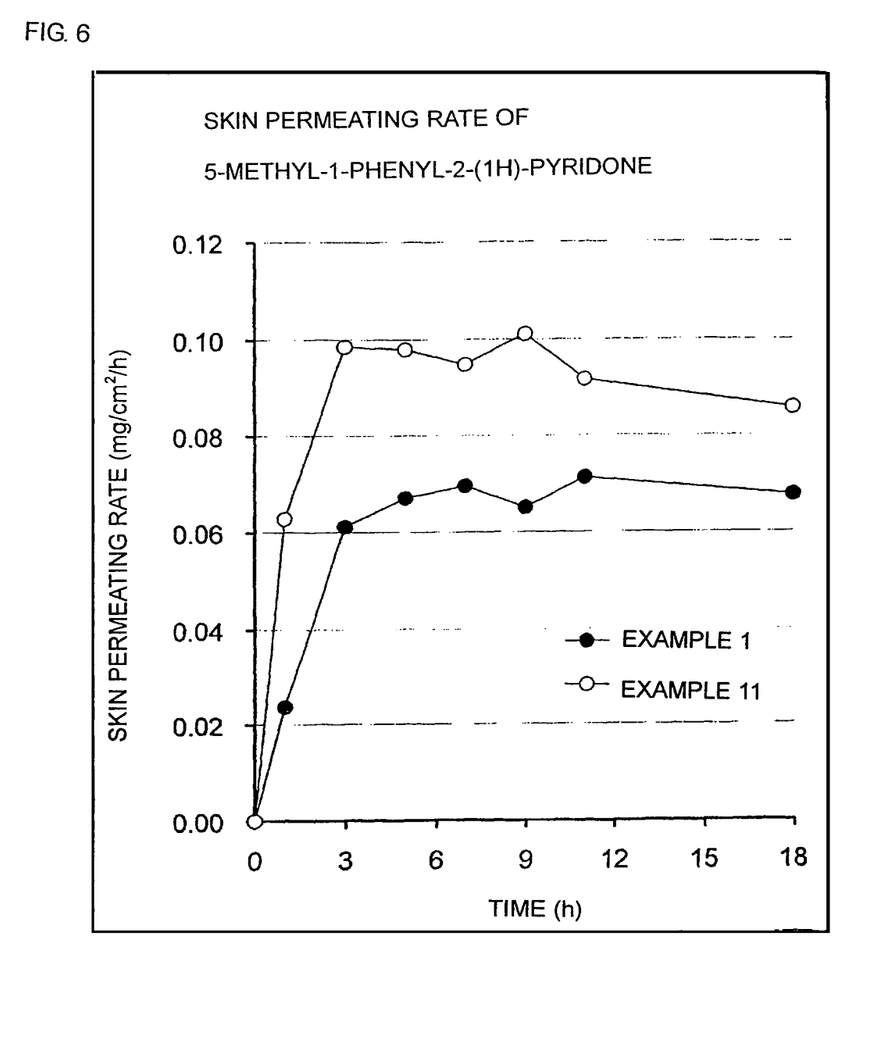
FIG. 6 is a graph showing a relationship between the elapsed time and the skin permeating rate after each of the PFD-containing adhesive preparations of Example 1 and Example 11 was applied to the skin of a rat.

As shown in FIG. 6, in comparison with the adhesive preparation of Example 1 containing no permeation enhancer, the adhesive preparation of Example 11 using, besides the dissolving agent of the present invention, a permeation enhancer exhibited a higher skin permeating rate.

Thus, it is expected that by using the specific dissolving agent of the present invention in combination with a permeation enhancer, the fast-acting property of the medicament (active medicinal ingredient) is further enhanced.

The invention claimed is:

1. A 5-methyl-1-phenyl-2-(1H)-pyridone-containing adhesive preparation including an active medicinal ingredient-containing layer, wherein:
    the active medicinal ingredient-containing layer contains a lipophilic base, a dissolving agent, and 5-methyl-1-phenyl-2-(1H)-pyridone or a medically acceptable salt thereof;
    the lipophilic base comprises: (i) at least one lipophilic polymer selected from the group consisting of styrene/isoprene/styrene block copolymers, styrene/butadiene block copolymers, polyisobutylene, polyisoprene, and polybutene; (ii) at least one plasticizer selected from the group consisting of liquid paraffin, vegetable oils, animal oils, vaseline, lanolin, and higher aliphatic esters; and (iii) at least one tackifier selected from the group consisting of petroleum resins, rosin-based resins, hydrogenated rosins, rosin esters, terpene resins, modified terpene resins, aromatic hydrocarbon resins, and aliphatic hydrocarbon resins; and
    the dissolving agent is selected from the group consisting of butylene glycol, polyethylene glycol, N-methyl-pyrrolidone, propylene carbonate, isopropyl myristate, crotamiton, and diisopropyl adipate.

2. The 5-methyl-1-phenyl-2-(1H)-pyridone-containing adhesive preparation according to claim 1, wherein the dissolving agent is selected from the group consisting of crotamiton and diisopropyl adipate.

3. The 5-methyl-1-phenyl-2-(1H)-pyridone-containing adhesive preparation according to claim 1, wherein the active medicinal ingredient-containing layer further contains a permeation enhancer.

4. The 5-methyl-1-phenyl-2-(1H)-pyridone-containing adhesive preparation according to claim 1, containing 5-methyl-1-phenyl-2-(1H)-pyridone or the medically acceptable salt thereof in an amount of 3 to 20% by mass, based on the total amount of the active medicinal ingredient-containing layer.

5. The 5-methyl-1-phenyl-2-(1H)-pyridone-containing adhesive preparation according to claim 2, wherein the active medicinal ingredient-containing layer further contains a permeation enhancer.

6. The 5-methyl-1-phenyl-2-(1H)-pyridone-containing adhesive preparation according to claim 2, containing 5-methyl-1-phenyl-2-(1H)-pyridone or the medically acceptable salt thereof in an amount of 3 to 20% by mass, based on the total amount of the active medicinal ingredient-containing layer.

7. The 5-methyl-1-phenyl-2-(1H)-pyridone-containing adhesive preparation according to claim 1, wherein the lipophilic base comprises at least two lipophilic polymers selected from the group consisting of styrene/isoprene/styrene block copolymers, styrene/butadiene block copolymers, polyisobutylene, polyisoprene, and polybutene.

8. The 5-methyl-1-phenyl-2-(1H)-pyridone-containing adhesive preparation according to claim 7, wherein the dissolving agent is selected from the group consisting of crotamiton and diisopropyl adipate.

9. The 5-methyl-1-phenyl-2-(1H)-pyridone-containing adhesive preparation according to claim 8, wherein the dissolving agent is in an amount ranging from 10% by mass to 20% by mass, based on the total amount of the active medicinal ingredient-containing layer.

10. The 5-methyl-1-phenyl-2-(1H)-pyridone-containing adhesive preparation according to claim 9, wherein the 5-methyl-1-phenyl-2-(1H)-pyridone or the medically acceptable salt thereof is in an amount of 3 to 20% by mass, based on the total amount of the active medicinal ingredient-containing layer.

11. The 5-methyl-1-phenyl-2-(1H)-pyridone-containing adhesive preparation according to claim 10, wherein the active medicinal ingredient-containing layer further comprises 1-menthol.

12. The 5-methyl-1-phenyl-2-(1H)-pyridone-containing adhesive preparation according to claim 1, wherein the dissolving agent is in an amount ranging from 10% by mass to 20% by mass, based on the total amount of the active medicinal ingredient-containing layer.

13. The 5-methyl-1-phenyl-2-(1H)-pyridone-containing adhesive preparation according to claim 2, wherein the dissolving agent is in an amount ranging from 10% by mass to 20% by mass, based on the total amount of the active medicinal ingredient-containing layer.

14. The 5-methyl-1-phenyl-2-(1H)-pyridone-containing adhesive preparation according to claim 3, wherein the permeation enhancer is 1-menthol.

15. The 5-methyl-1-phenyl-2-(1H)-pyridone-containing adhesive preparation according to claim 5, wherein the permeation enhancer is 1-menthol.

\* \* \* \* \*